United States Patent [19]

Madhusudhan et al.

[11] Patent Number: 5,168,746

[45] Date of Patent: Dec. 8, 1992

[54] AMBIENT ETHER VAPOR TESTING APPARATUS AND METHOD

[75] Inventors: Chilengi P. Madhusudhan, Torrance; Joaquin M. Otero, Carson, both of Calif.

[73] Assignee: Hughes Aircraft Company, Los Angeles, Calif.

[21] Appl. No.: 709,262

[22] Filed: Jun. 3, 1991

[51] Int. Cl.$^5$ ............................................. G01N 30/08
[52] U.S. Cl. ................................................. 73/23.35
[58] Field of Search ................ 73/23.35, 23.41, 31.02; 340/632

[56] References Cited

U.S. PATENT DOCUMENTS

| | | | |
|---|---|---|---|
| 3,053,077 | 9/1962 | Tracht | 73/23.41 X |
| 3,427,863 | 2/1969 | Schultz | 73/23.35 X |
| 4,042,326 | 8/1977 | Kallos | 73/23.41 X |
| 4,185,490 | 1/1980 | Clouser et al. | 73/23.35 |

FOREIGN PATENT DOCUMENTS 370401  5/1990  European Pat. Off. ........... 73/23.35

Primary Examiner—Hezron E. Williams
Assistant Examiner—Joseph W. Roskos
Attorney, Agent, or Firm—L. A. Alkov; W. K. Denson-Low

[57] ABSTRACT

A portion of the ambient air, including the selected vapor such as the ether vapor fraction, is first cryogenically liquefied for concentration in a collecting vessel (12). Thereafter, the concentrated liquefied fraction is boiled off and passed through gas chromatography column (34) to separate the fractions in the vapor stream. The selected vapor fraction is eluted at the temperature, and its concentration is detected by thermal conductivity detector (42) so that the concentration of the selected vapor in the environment is signaled.

12 Claims, 1 Drawing Sheet

AMBIENT ETHER VAPOR TESTING APPARATUS AND METHOD

FIELD OF THE INVENTION

This invention is directed to the testing of the ambient atmosphere for diethyl ether vapor and other organic solvents such as esters, ethers and the like, including both apparatus and method.

BACKGROUND OF THE INVENTION

Diethyl ether, commonly simply called "ether," is used as an inhalation anaesthetic in hospitals. It is used in industry as a solvent for waxes, fats, oils, and perfumes. It is used in the synthesis of controlled substances such as cocaine. It is used as a reagent in organic synthesis. It is used in the manufacture of gunpowder, and it is used as a primer for internal combustion engines.

Ether vapor is a preferred example of an organic solvent vapor and is heavier than air and is highly flammable. Air-ether mixtures containing more than 1.85 percent by volume of ether vapor are explosive hazards. Autoignition temperature of such mixtures is about 180 degrees C. In the interest of safety, it would be helpful to be able to monitor ether vapors with a real-time apparatus and method for use in places like hospital rooms and industrial environments where ether is used. Such an apparatus and method can also be used in drug law enforcement to detect emission of solvents. A suitable testing apparatus and method will help monitor the ether concentration and warn the personnel about dangerous ether vapor buildups to permit control of the ether vapor before dangerous levels occur. Another utility for a real time organic vapor sensor is in protection against chemical warfare agents.

One commercially available device which monitors ether is a gas detection tube made by Matheson Gas Products, which is a division of Global Occupational Safety of Hempstead, N.Y. These gas detection tubes are filled with chemical reagents. When ambient air is drawn through the tubes, the chemical reagent changes color in the presence of the suspected vapor. The amount of color change is proportional to the concentration in the sample, and this is compared to a printed chart. This gas detection tube system requires a long sampling period so that it does not give substantially real-time results. Additionally, there is a limited shelf life associated with such gas detection tubes. Another disadvantage is that it is of questionable accuracy in the measurement of the concentration of ether in the ambient air. In addition, no warning signal is given. Accordingly, there is a need for an apparatus and method which provides substantially real-time information as to the amount of ether or other specific vapor in the ambient air.

SUMMARY OF THE INVENTION

In order to aid in the understanding of this invention, it can be stated in essentially summary form that it is directed to a method and apparatus for the testing for ether vapor in the ambient air. The apparatus comprises a cryogenic concentrator to concentrate a sample and includes a chromatographic column which separates the sample. Upon separation and elution, the thermal conductivity detector signals the ether vapor concentration. Testing levels in the parts-per-million range are achieved. The method comprises the steps of concentrating, separating and detecting ether concentrations.

It is thus a purpose and advantage of this invention to provide an apparatus for the testing of ether vapor in the ambient air.

It is another purpose and advantage of this invention to provide an apparatus which is capable of testing for the ambient ether vapor in the parts-per-million range so that the vapor can be detected before the concentration becomes dangerous.

It is another purpose and advantage of this invention to provide an ambient ether vapor testing apparatus which employs gas chromatography for separating ether vapor so that it can be measured.

It is a further purpose and advantage of this invention to provide a method for the testing of ether vapor in the ambient air.

It is another purpose and advantage of this invention to provide a method which is capable of testing for the ambient ether vapor in the parts-per-million range so that the vapor can be detected before the concentration becomes dangerous.

It is another purpose and advantage of this invention to provide an ambient ether vapor testing method which employs gas chromatography for separating ether vapor so that it can be measured.

Other purposes and advantages of this invention will become apparent from a study of the following portion of the specification, the claims and the attached drawings wherein:

DESCRIPTION OF THE PREFERRED EMBODIMENT

Figure 1:
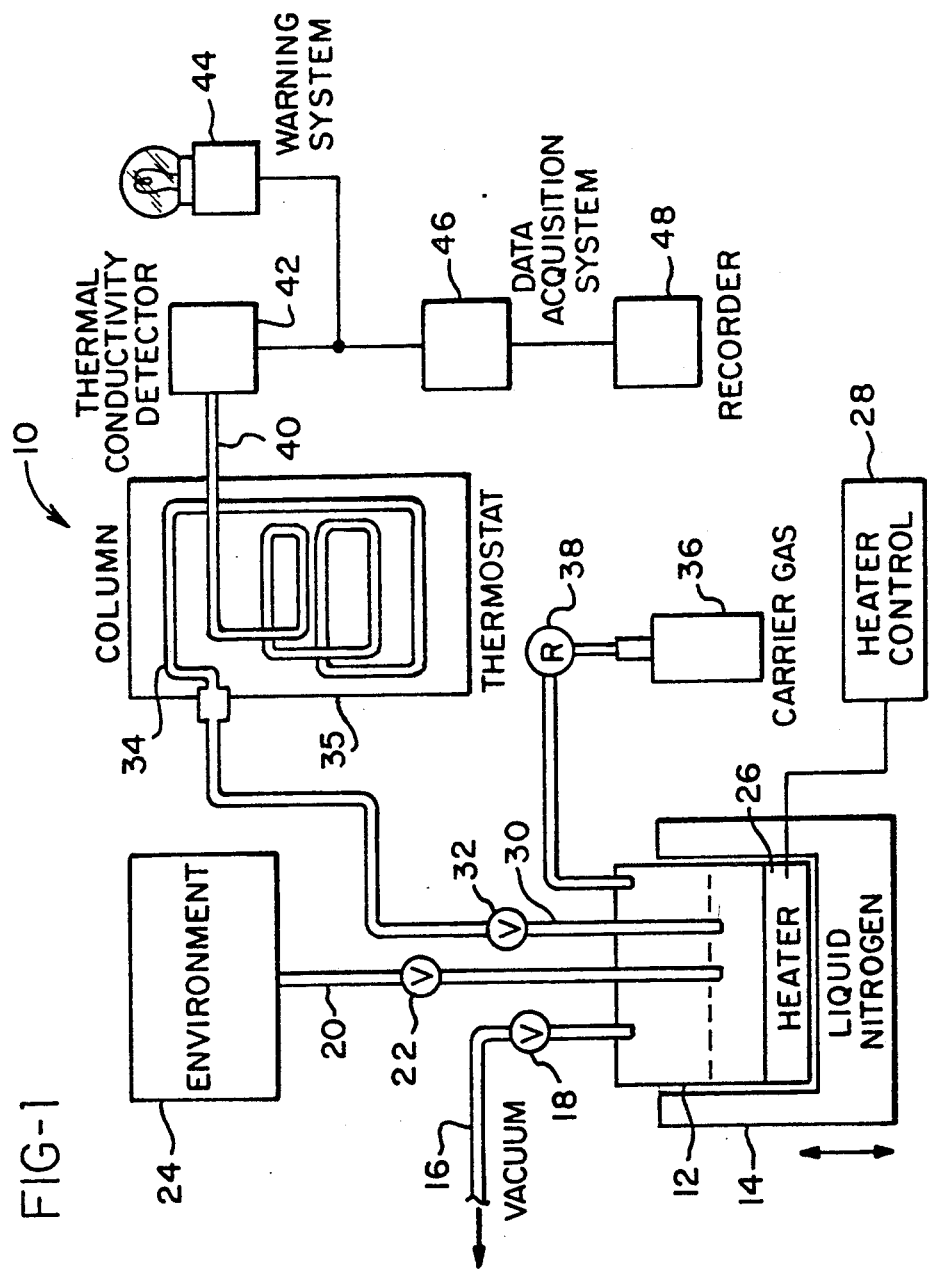
FIG. 1 is a schematic diagram of the apparatus of this invention.

The ambient ether vapor testing apparatus is generally indicated at 10 in FIG. 1. It comprises a concentrator, a gas chromatographic separator and a detector. Going through the apparatus 10 in the direction of flow and cycle operation, it has a collecting vessel 12. The collecting vessel is cooled by a liquid nitrogen Dewar 14 which is at least insulated on its exterior, with the interior of the Dewar sized to receive the vessel 12. The Dewar is removable from the position shown where it is cooling vessel 12 to a lowered position where it is away from vessel 12. In the first part of the cycle, the Dewar is in place, a vacuum is drawn on suction line 16, and suction valve 18 is opened. Sample line 20 is connected to vessel 12 through sample valve 22. With the sample valve 22 open, mixed gases, principally air, are drawn from the environment 24. The environment 24 is the location where the diethyl ether vapor is suspected. Thus, it is a hospital room, a facility in which diethyl ether is manufactured, or a facility in which diethyl ether is used. The ambient gas mixture drawn from the environment 24 is principally air, which, in turn, is a mixture of gases, principally nitrogen and oxygen. Other constituents in the air include the rare gases and carbon dioxide. Other gases and vapors in the air are considered pollutants. As this gas mixture moves through the sample line 20 into vessel 12, it is selectively liquefied. The liquid nitrogen in the Dewar boils at −195.8 degrees C. and, thus, condenses out of the sample stream some of the rare gases, oxygen, the carbon dioxide, and many of the pollutants, including diethyl ether vapor. Thus, the liquid collected in vessel 12 is principally oxygen, carbon dioxide, some rare gases and pollutants such as ether boiling above about −196 degrees C. This sample collecting can be run over a fairly long period, say several hours, or may be run over a short period, say 10 minutes, depending upon the sample timing desired.

When the collecting step is completed, suction valve 18 and sample valve 22 are closed. In addition, the liquid nitrogen Dewar 14 is removed. The liquid sample in vessel 12 is boiled off. Heater 26 is connected to the collecting vessel 12 to add heat for the boil-off step. Heater 26 is controlled by controller 28. Concentrate line 30 is connected through concentrate valve 32 to gas chromatography column 34. To aid in carrying the boiling concentrate through the column, carrier gas supply tank 36 delivers carrier gas to the vessel 12 through pressure regulator 38. The pressure regulator controls the flow rate of the carrier gas. The preferred carrier gas is helium. The carrier gas plus the boiling-off concentrate are delivered to column 34.

Figure 2:
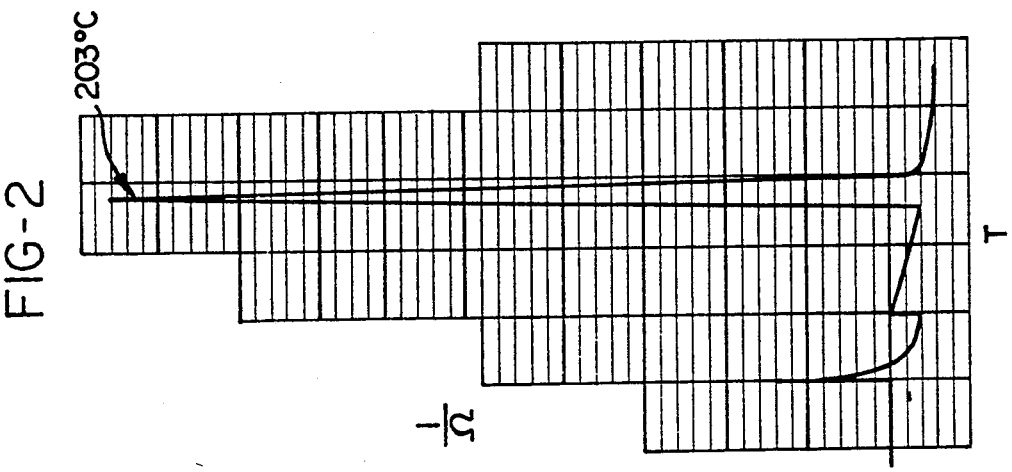
FIG. 2 is a graph showing an ether vapor peak as the concentrated materials are boiled off.

Column 34 is a Porapak Q gas chromatography column supplied by Water Associates U.S.A. The column contains a 6-foot long ⅛ inch diameter tube. Column 34 is housed in an insulated cover 35 which also contains a thermostatically controlled heater. As the temperature of the column is raised, at 203 degrees C. the ether vapors that have been adsorbed on the column surface are eluted out of the column and led into the thermal conductivity detector. The column 34 has its own heating element which heats the column to the desired temperature, such as 203 degrees C. to elute either vapor. The temperature indicated in FIG. 2 is the temperature of the column 34 which is 203 degrees C. in this specific example.

As the collecting vessel 12 is warmed up and as the column 34 is warmed up, different fractions come through the column. The components which form these different fractions are delivered by outlet line 40 to detector 42. Detector 42 is a thermal conductivity detector. When the thermal conductivity is related to the temperature of the incoming gas in outlet line 40, conductivity peaks signal different concentrations of different fractions. A relatively simple and broadly applicable detection system is based upon the thermal conductivity of the gas stream. The sensing element is an electrically heated source whose temperature at constant electrical power depends on the thermal conductivity of the surrounding gas. The heated element may consist of a fine platinum or tungsten wire. The resistance of the wire gives a measure of the thermal conductivity of the gas—ether in the particular example. A particular thermal conductivity detector useful for this testing is a Varian Model 3700GC. FIG. 2 shows a conductivity peak at a temperature of 203 degrees C. In FIG. 2, the vertical scale is the detector signal, while the horizontal scale is the time. The height and width of this peak shows the concentration of diethyl ether vapor in the sample. The output of the thermal conductivity detector 42 goes to a warning system 44 which emits a signal when concentration rises above a set point. Additionally, the output of detector 42 goes to a data acquisition system 46.

An example of a data acquisition system is Optomux (Mfr., OPTO-22, Huntington Beach, Calif.). This system takes input from a detector (such as from a thermal conductivity detector) and feeds into a computer. Suitable computer programs can be developed to store data (such as the concentration of ether on a certain day at a certain time) and generate data as and when required. Recorder 48 maintains a record of the results. In this way, concentration of diethyl ether in the environment is tested, recorded and, when above a predetermined set point, a signal is emitted. Both qualitative and quantitative information on ether can be obtained.

At the end of the cycle, the heater 26 is turned off by controller 28, valves 32 and 38 are closed, the liquid nitrogen Dewar 14 is replaced to cool vessel 12, and thereupon, valves 18 and 22 are opened to begin a new cycle of concentration. Cycling can be as fast as desired, particularly depending upon the rate at which heating and cooling can be achieved.

This invention having been described in its presently contemplated best mode, it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A testing apparatus for testing for a selected vapor comprising:
   an air fractionating concentrator collecting vessel having an environmental gas inlet, an uncondensed gas outlet and a concentrated gas outlet;
   means for refrigerating said vessel to subliquid air temperature so that a portion of the environmental gas is liquefied to form a concentrated liquid;
   a heater connected to said vessel for subsequently heating said environmental liquid collecting vessel to boil off the concentrated liquid therein;
   means for separating the selected vapor resulting from said boiling liquid; and
   means for detecting the selected vapor in a fraction from said means for separating.

2. The apparatus of claim 1 wherein said means for separating is a gas chromatography column.

3. The apparatus of claim 1 wherein said means for detecting is a thermal conductivity detector.

4. The apparatus of claim 3 wherein said means for separating is a gas chromatography column.

5. The apparatus of claim 3 wherein a warning system is connected to said detector to emit a warning when concentration of the selected vapor in the environment exceeds a predetermined value.

6. An ambient ether vapor testing apparatus comprising:
   a liquid sample collecting vessel;
   a supply tube for passing environmental air, including its contaminants, to said collecting vessel, said collecting vessel being larger than said supply tube;
   means for cooling said collecting vessel so that a portion of the contaminants, including ether, is condensed in said collecting vessel;
   a removal tube connected to said collecting vessel for removing from said vessel the uncondensed portion of the environmental air from said collecting vessel;
   means for removing said cooling means and a heater connected to said vessel for heating said collecting vessel to boil off contaminants collected in and concentrated in said collecting vessel;
   a gas chromatography column for separating boiled-off vapor into fractions as a function of temperature so that the fraction containing ether vapor can be determined by temperature; and a thermal conductivity detector for testing the ether vapor fraction to determine the concentration of ether in the ether vapor fraction to detect the amount of ether vapor in the environment.

7. The apparatus of claim 6 further including a warning system for emitting a signal when said thermal conductivity detector detects an ether vapor concentration indicating dangerous levels of ether vapor in the environment.

8. The apparatus of claim 7 further including means for recording the output of said thermal conductivity detector.

9. The apparatus of claim 6 further including a carrier gas system to carry boiled-off vapors through said column.

10. The apparatus of claim 9 wherein said carrier gas supply system is a helium gas supply system.

11. The method for testing for a selected vapor comprising the steps of:

drawing ambient air and contaminants into a collecting and concentrating vessel which is cooled to a temperature below the boiling point of the selected vapor to liquefy the selected vapor and at the same time drawing air with a lower concentration of contaminants out of the collecting and concentrating vessel;

subsequently to liquefying the selected vapor in the collecting vessel, heating the collecting vessel to boil off the liquefied ambient air and contaminants therein to form a vapor;

passing the vapor through a gas chromatography column to separate the air and contaminant fractions; and detecting and measuring the selected vapor fraction as a function of thermal conductivity and temperature so that the amount of selected vapor in the ambient atmosphere is signaled.

12. The method of claim 11 further including emitting a warning signal when the detected level of the selected vapor represents a dangerous level of the selected vapor in the ambient air.

* * * * *